US012642988B2

(12) United States Patent
Kim et al.

(10) Patent No.: US 12,642,988 B2
(45) Date of Patent: Jun. 2, 2026

(54) DEVICE FOR RELIEVING DEMENTIA SYMPTOMS

(71) Applicants: N.CER Co., Ltd, Gwangju (KR); GWANGJU INSTITUTE OF SCIENCE AND TECHNOLOGY, Gwangju (KR)

(72) Inventors: Jae won Kim, Gwangju (KR); Jae Gwan Kim, Gwangju (KR); Jeong Dae Yun, Seoul (KR); Sung Chul Kim, Gwangju (KR)

(73) Assignees: N.CER Co., Ltd, Gwangju (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 166 days.

(21) Appl. No.: 18/825,145

(22) Filed: Sep. 5, 2024

(65) Prior Publication Data

US 2025/0018218 A1    Jan. 16, 2025

Related U.S. Application Data

(63) Continuation-in-part of application No. 18/198,992, filed on May 18, 2023, now abandoned, which is a
(Continued)

(30) Foreign Application Priority Data

Nov. 19, 2020    (KR) ........................ 10-2020-0155260

(51) Int. Cl.
*A61N 5/06* (2006.01)
(52) U.S. Cl.
CPC .... *A61N 5/0622* (2013.01); *A61N 2005/0626* (2013.01); *A61N 2005/0648* (2013.01);
(Continued)

(58) Field of Classification Search
CPC .... A61N 2005/0626; A61N 2005/0647; A61N 2005/0648; A61N 2005/0659;
(Continued)

(56) References Cited

U.S. PATENT DOCUMENTS 10,660,524 B2    5/2020  Dubielczyk et al.
11,590,313 B2    2/2023  Lee
(Continued)

FOREIGN PATENT DOCUMENTS

EP        0747080 A1    12/1996
JP    2018-511371 A     4/2018
(Continued)

OTHER PUBLICATIONS

Office Action of Korean Patent Application No. 10-2020-0155260 issued Jul. 20, 2021.
(Continued)

*Primary Examiner* — Amanda K Hulbert
(74) *Attorney, Agent, or Firm* — Dinsmore & Shohl LLP; Yongsok Choi, Esq.

(57) ABSTRACT

A device for relieving dementia symptoms is disclosed. The device for relieving dementia symptoms includes a light stimulation part disposed at a location within a preset radius from an eyeball and frontal lobe of a patient and configured to relieve dementia symptoms of the patient by radiating light having a preset wavelength band to an optic nerve and frontal lobe of the patient, and a central processing unit configured to control an operation of the light stimulation part.

8 Claims, 3 Drawing Sheets

Related U.S. Application Data continuation of application No. PCT/KR2021/016765, filed on Nov. 16, 2021.

(52) U.S. Cl.
CPC ................. *A61N 2005/0659* (2013.01); *A61N 2005/0663* (2013.01)

(58) Field of Classification Search
CPC .... A61N 2005/0662; A61N 2005/0663; A61N 5/0618; A61N 5/0622
See application file for complete search history.

(56) References Cited

U.S. PATENT DOCUMENTS

| | | |
|---|---|---|
| 11,730,917 B2 | 8/2023 | Carstensen |
| 11,738,207 B2 | 8/2023 | Cassano |
| 2016/0067087 A1 | 3/2016 | Tedford |
| 2021/0205634 A1* | 7/2021 | Sverdlov .............. A61N 5/0622 |
| 2021/0275827 A1* | 9/2021 | Barron ................. A61N 5/0618 |
| 2021/0339043 A1 | 11/2021 | Malchano |

FOREIGN PATENT DOCUMENTS

| | | |
|---|---|---|
| JP | 2018-166568 A | 11/2018 |
| JP | 2019-053625 A | 4/2019 |
| KR | 1020170096856 A | 8/2017 |
| KR | 1020200056984 A | 5/2020 |
| KR | 1020200070300 A | 6/2020 |
| KR | 1020200127521 A | 11/2020 |
| WO | 2016151377 A1 | 9/2016 |

OTHER PUBLICATIONS

Abay, T. Y., Kyriacou, P. A. (2017). Photoplethysmography for blood vols. and oxygenation changes during intermittent vascular occlusions. Journal of Clinical Monitoring and Computing, 32(3), 447-455. https://doi.org/10.1007/S10877-017-0030-2 (Year: 2017).

* cited by examiner (a)

(b)

DEVICE FOR RELIEVING DEMENTIA SYMPTOMS

CROSS-REFERENCE TO RELATED APPLICATIONS

The present application is a continuation-in-part of U.S. patent application Ser. No. 18/198,992, which is a continuation of International Application No. PCT/KR2021/016765 filed on Nov. 16, 2021 which claims priority under 35 U.S.C. § 119(a) to Korean application number 10-2020-0155260, filed in the Korean Intellectual Property Office on Nov. 19, 2020, the entire disclosure of which is incorporated herein by reference.

BACKGROUND

1. Technical Field

The present disclosure relates to a device capable of relieving dementia symptoms of a patient.

2. Related Art

Contents described in this part merely provide background information of the present embodiment, and do not constitute a conventional technology.

Dementia is a disease that reduces the elasticity of a blood vessel or causes a hormone problem due to a decrease in the brain function. Due to the above problem, a dementia patient has decreased memory or a decreased cognitive function, such as intelligence, learning, or a language.

In order to relieve such dementia symptoms, conventionally, relievers have been developed in the form of a medicine which may be taken by a patient. A medicine for reducing beta amyloid protein that has been known to cause dementia has been developed. However, such conventional medicines have not played a sufficient role in relieving symptoms of a dementia patient because the medicines have limits in relieving the dementia symptoms.

For this reason, various digital devices have emerged in order to relieve symptoms of a dementia patient. The digital device is mounted on the body of the patient in order to relieve the dementia symptoms by improving the brain function. However, it is very difficult for a dementia patient to maintain an environment in which the dementia patient has a treatment effect because the dementia patient has to have a corresponding device mounted on the body of the dementia patient and to continuously watch an output screen that is provided by the device. Due to such problems, there is no proper method of relieving dementia symptoms conventionally.

SUMMARY

An embodiment of the present disclosure is directed to a device for relieving dementia symptoms, which is mounted on the body of a patient without inconvenience and can relieve dementia symptoms of a patient.

According to an aspect of the present disclosure, a device for relieving dementia symptoms includes a light stimulation part disposed at a location within a preset radius from an eyeball and frontal lobe of a patient and configured to relieve dementia symptoms of the patient by radiating light having a preset wavelength band to an optic nerve and frontal lobe of the patient, and a central processing unit configured to control an operation of the light stimulation part.

According to an aspect of the present disclosure, the preset wavelength band is a near-infrared ray wavelength band.

According to an aspect of the present disclosure, the light stimulation part includes a first light stimulation part configured to radiate light having a wavelength band within a preset range on the basis of 730 nm, and a second light stimulation part configured to radiate light having a wavelength band within a preset range on the basis of 850 nm.

According to an aspect of the present disclosure, the light stimulation part radiates light having a preset frequency band.

According to an aspect of the present disclosure, the device for relieving dementia symptoms further includes an acoustic stimulation part configured to provide the patient with a sonorant having a preset frequency band.

According to an aspect of the present disclosure, the preset frequency band is a gamma frequency band.

According to an aspect of the present disclosure, the central processing unit is capable of changing the frequency band of the light radiated by the light stimulation part into a second preset frequency band.

According to an aspect of the present disclosure, the device for relieving dementia symptoms further includes a first light-receiving part disposed within a preset radius from the light stimulation part and configured to receive light that is radiated to have the second preset frequency band from the light stimulation part and that is reflected by an artery within a skin of the patient.

According to an aspect of the present disclosure, the central processing unit measures a heart rate and oxygen saturation of the patient based on information received by the first light-receiving part.

According to an aspect of the present disclosure, the device for relieving dementia symptoms further includes a second light-receiving part disposed outside a preset radius from the light stimulation part and configured to receive light that is radiated to have the second preset frequency band from the light stimulation part and that is reflected by the frontal lobe of the patient.

According to an aspect of the present disclosure, the central processing unit measures a patient's brain oxygen saturation based on information received by the second light-receiving part.

According to an aspect of the present disclosure, the second light-receiving part is included in a plural number.

As described above, according to an aspect of the present disclosure, the device for relieving dementia symptoms can be mounted on the body of the patient without inconvenience. Accordingly, it is possible to provide a symptom relief effect because the device is mounted on the body of a patient for a desired time because the device.

Furthermore, according to an aspect of the present disclosure, the device for relieving dementia symptoms can provide an excellent dementia symptom relief effect by stimulating a patient through both light and a sound.

DETAILED DESCRIPTION

Figure 1:
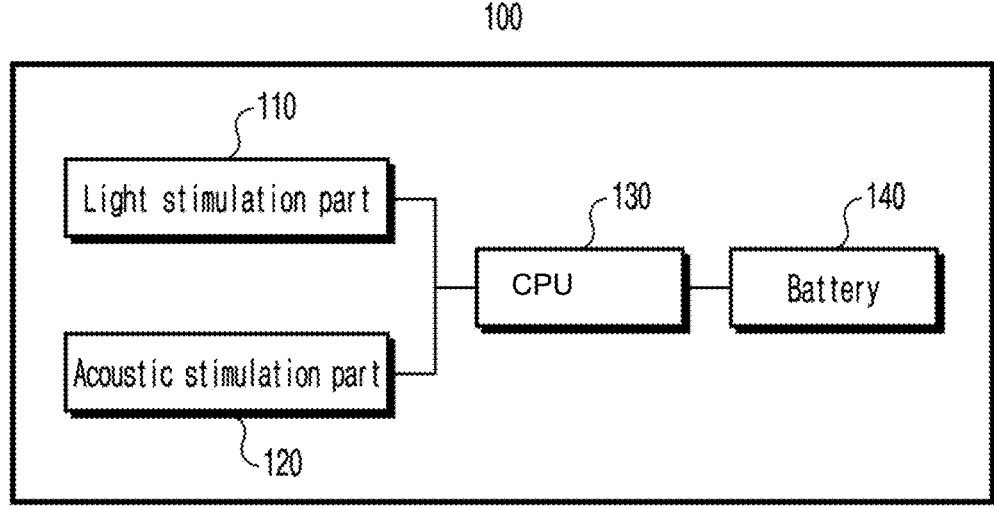
FIG. 1 is a diagram illustrating a construction of a device for relieving dementia symptoms according to a first embodiment of the present disclosure.

The present disclosure may be changed in various ways and may have various embodiments. Specific embodiments are to be illustrated in the drawings and specifically described. It should be understood that the present disclosure is not intended to be limited to the specific embodiments, but includes all of changes, equivalents and/or substitutions included in the spirit and technical range of the present disclosure. Similar reference numerals are used for similar components while each drawing is described.

Terms, such as a first, a second, A, and B, may be used to describe various components, but the components should not be restricted by the terms. The terms are used to only distinguish one component from another component. For example, a first component may be referred to as a second component without departing from the scope of rights of the present disclosure. Likewise, a second component may be referred to as a first component. The term "and/or" includes a combination of a plurality of related and described items or any one of a plurality of related and described items.

When it is described that one component is "connected" or "coupled" to the other component, it should be understood that one component may be directly connected or coupled to the other component, but a third component may exist between the two components. In contrast, when it is described that one component is "directly connected to" or "directly coupled to" the other component, it should be understood that a third component does not exist between the two components.

Terms used in this application are used to only describe specific embodiments and are not intended to restrict the present disclosure. An expression of the singular number includes an expression of the plural number unless clearly defined otherwise in the context. In this specification, a term, such as "include" or "have", is intended to designate the presence of a characteristic, a number, a step, an operation, a component, a part or a combination of them, and should be understood that it does not exclude the existence or possible addition of one or more other characteristics, numbers, steps, operations, components, parts, or combinations of them in advance.

All terms used herein, including technical terms or scientific terms, have the same meanings as those commonly understood by a person having ordinary knowledge in the art to which the present disclosure pertains, unless defined otherwise in the specification.

Terms, such as those defined in commonly used dictionaries, should be construed as having the same meanings as those in the context of a related technology, and are not construed as ideal or excessively formal meanings unless explicitly defined otherwise in the application.

Furthermore, each construction, process, procedure, or method included in each embodiment of the present disclosure may be shared within a range in which the constructions, processes, procedures, or methods do not contradict each other technically.

FIG. 1 is a diagram illustrating a construction of a device for relieving dementia symptoms according to a first embodiment of the present disclosure.

Referring to FIG. 1, a device 100 for relieving dementia symptoms according to the first embodiment of the present disclosure includes a light stimulation part 110, an acoustic stimulation part 120, and a central processing unit 130. The device 100 for relieving dementia symptoms may further include a battery 140. The device 100 may be any mobile device, such as a wearable device. The central processing unit 130 may be a controller, an integrated circuit, a microchip, a computer, or any other computing device.

The device 100 may include memory modules. The memory modules may comprise RAM, ROM, flash memories, hard drives, or any device capable of storing machine-readable and executable instructions such that the machine-readable and executable instructions can be accessed by the central processing unit 130.

The memory modules stores instructions that, when executed by the central processing unit 130, instruct the central processing unit 130 to perform functions described in the present disclosure such as controlling an operation of the first light stimulation part 110, a second light stimulation part 310, and the acoustic stimulation part 120 and synchronizing an optical signal that is output by the first and second light stimulation parts 110 and 310 and an acoustic signal that is output by the acoustic stimulation part 120.

The instructions may comprise one or more logic or algorithms written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine-readable and executable instructions and stored on the one or more memory components 202. Alternatively, the machine-readable and executable instructions may be written in a hardware description language (HDL), such as logic implemented via either a field-programmable gate array (FPGA) configuration or an application-specific integrated circuit (ASIC), or their equivalents.

The device 100 for relieving dementia symptoms is mounted on the body of a dementia patient, and it provides an optical signal and an acoustic signal and relieves dementia symptoms of the patient. Some research results reveal that when the brain of a patient, in particular, the frontal lobe is stimulated by a sound or light having a specific frequency band, the cognitive function of the brain is improved. Accordingly, the device 100 for relieving dementia symptoms is mounted on the body of a patient, and can relieve dementia symptoms by improving the cognitive function of the patient in a way to stimulate the frontal lobe and optic nerve of the patient through an optical signal and to simultaneously stimulate the patient's brain through an acoustic signal.

The light stimulation part 110 stimulates the optic nerve and frontal lobe of a patient by radiating light having a near-infrared ray wavelength band. The light stimulation part 110 is mounted on the body of a patient within a preset radius from both the optic nerve and frontal lobe of the patient, and applies light having the near-infrared ray wavelength band to the patient. For example, a location at which the light stimulation part 110 is disposed may be the middle of the forehead or a portion that neighbors the middle of the forehead, within a preset radius from both the optic nerve and frontal lobe of a patient. The light stimulation part 110 is mounted on a corresponding portion of a patient, and radiates light having the near-infrared ray wavelength band. The light having the near-infrared ray wavelength band can reach an optic nerve within the skin or the frontal lobe through the skin. Accordingly, the patient does not need to watch light that is radiated by the light stimulation part 110 or the light stimulation part 110. Although the patient closes his or her eyes, the light stimulation part 110 can stimulate the optic nerve and frontal lobe of the patient.

The light stimulation part 110 radiates light having the near-infrared ray wavelength band in order to stimulate the optic nerve and frontal lobe of a patient. The light stimulation part 110 may include two or more light sources. A wavelength band that stimulates the optic nerve is about 730 nm. A wavelength band that stimulates the frontal lobe is about 850 nm. In order to stimulate both the optic nerve and the frontal lobe, the light stimulation part 110 includes two or more light sources, and radiates light having a wavelength band of about 730 nm and light having a wavelength band of about 850 nm.

The light stimulation part 110 radiates light having the near-infrared ray wavelength band in the form of a preset frequency under the control of the central processing unit 130. In this case, the preset frequency may be a gamma frequency band, that is, 30 to 50 Hz. The light and sound of the gamma frequency band reduces beta amyloid protein related to dementia symptoms. In particular, light having the gamma frequency band increases microglia, that is, a cell that reduces such beta amyloid protein. The light stimulation part 110 can improve the cognitive function of a patient through the reduction of beta amyloid (by inducing an increase in microglia) by radiating light having corresponding frequencies to the optic nerve and frontal lobe of the patient.

The acoustic stimulation part 120 stimulates the patient's brain by outputting a sonorant having a preset frequency. Like the light stimulation part 110, the acoustic stimulation part 120 radiates the sonorant having a gamma frequency band (30 to 50 Hz). Accordingly, the acoustic stimulation part 120 can relieve dementia symptoms by reducing beta amyloid protein.

The central processing unit 130 controls operations of the light stimulation part 110 and the acoustic stimulation part 120.

The central processing unit 130 controls the light stimulation part 110 to output an optical signal and the acoustic stimulation part 120 to output an acoustic signal. In this case, the central processing unit 130 controls the light stimulation part 110 and the acoustic stimulation part 120 so that both the light stimulation part 110 and the acoustic stimulation part 120 output signals each having a frequency having a preset frequency band (a gamma frequency band) by frequency modulation.

The central processing unit 130 controls signal output timing of the light stimulation part 110 and the acoustic stimulation part 120. The central processing unit 130 controls the light stimulation part 110 to alternately output an optical signal (e.g., an optical signal having a wavelength band of about 730 nm) that stimulates the optic nerve of a patient and an optical signal (e.g., an optical signal having a wavelength band of about 850 nm) that stimulates the frontal lobe of the patient. At the same time, the central processing unit 130 controls the acoustic stimulation part 120 to output an acoustic signal in synchronization with arbitrary timing from timing at which the optical signal that stimulates the optic nerve is output to timing at which the optical signal that stimulates the frontal lobe is output. As the optical signal and the acoustic signal are synchronized with each other and applied to the patient, a dementia symptom relief effect can become better. The optical signal and the acoustic signal output timing of which is controlled by the central processing unit 130 are illustrated in FIGS. 5A and 5B.

Figure 5A:
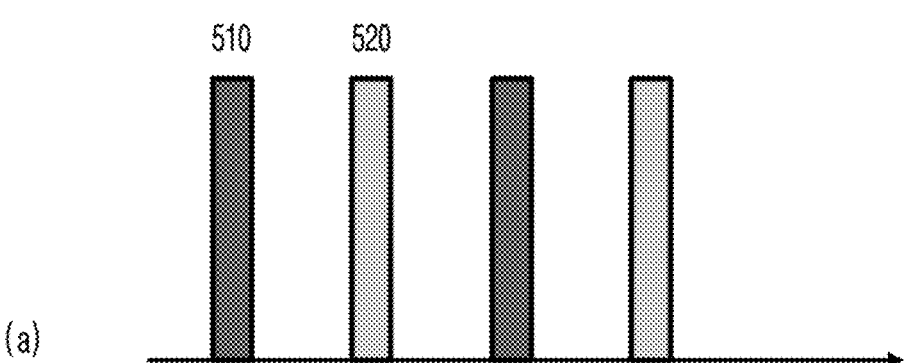
FIGS. 5A and 5B are graph illustrating an optical signal and an acoustic signal that are output by the device for relieving dementia symptoms according to an embodiment of the present disclosure.
Figure 5B:
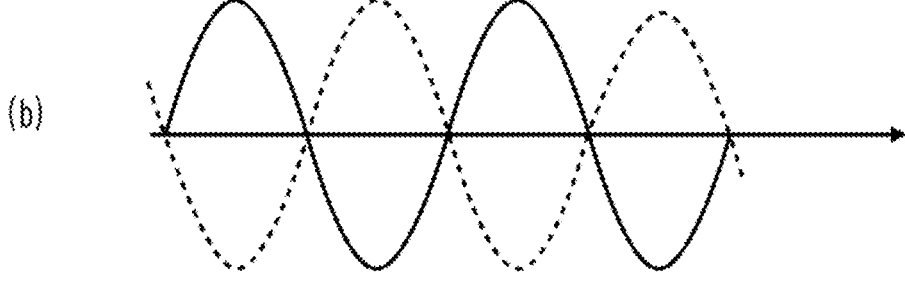

FIGS. 5A and 5B are graphs illustrating an optical signal and an acoustic signal that are output by the device for relieving dementia symptoms according to an embodiment of the present disclosure.

Referring to FIG. 5A, the light stimulation part 110 alternately outputs an optic nerve stimulation signal 510 and a frontal lobe stimulation signal 520. Each of the signals 510 and 520 is output with a gamma frequency band.

Referring to FIG. 5B, the acoustic stimulation part 120 outputs an acoustic signal having a gamma frequency band simultaneously with an optical signal. The phase of the acoustic signal may be adjusted within 90 degrees under the control of the central processing unit 130. That is, a positive peak point of the acoustic signal may have a phase that is synchronized with the optic nerve stimulation signal 510, may have a phase that is synchronized with the frontal lobe stimulation signal 520, and may have a phase between the phase synchronized with the optic nerve stimulation signal 510 and the phase synchronized with the frontal lobe stimulation signal 520. In this case, the adjusted phase of the acoustic signal may be different depending on an aspect of dementia symptoms of a patient.

Referring back to FIG. 1, the battery 140 provides power that enables each of the components of the device 100 for relieving dementia symptoms to operate. The device 100 for relieving dementia symptoms may include a (wired) plug (not illustrated) that is electrically connected to a commercial power supply, without including the battery 140. However, if the device 100 for relieving dementia symptoms includes the plug, a behavior of a dementia patient may be limited. For this reason, the battery 140 may be included in the device 100 for relieving dementia symptoms, and may supply power.

Figure 2:
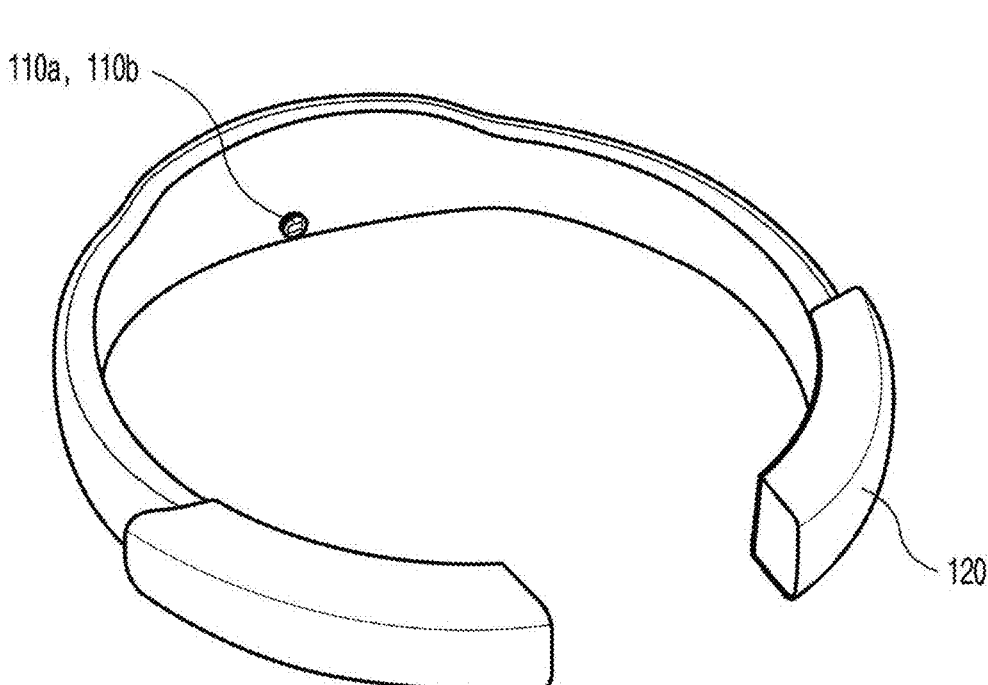
FIG. 2 is an exemplary diagram of a device for relieving dementia symptoms according to a first embodiment of the present disclosure.

FIG. 2 is an exemplary diagram of a device for relieving dementia symptoms according to a first embodiment of the present disclosure.

As illustrated in FIG. 2, the device 100 for relieving dementia symptoms may be implemented in the form of a headset that is mounted on the forehead and ears of a patient. When the device is mounted on the body of a patient, light stimulation parts 110a and 110b are disposed in the middle of the forehead of the patient or a portion with which a middle part of the forehead will come into, and output optical signals to the optic nerve and frontal lobe of the patient, respectively. Accordingly, the patient has only to mount the light stimulation parts 110a and 110b on his or her body, and can have a symptom relief effect by receiving the optical signals without the need to separately watch the light stimulation parts 110a and 110b.

When the device is mounted on the body of a patient, the acoustic stimulation part 120 is disposed at the ears of the patient or in parts around the ears, and provides an acoustic signal to the patient. The acoustic stimulation part 120 may be implemented as an earphone, but the earphone may provide a bad feeling of wearing to a dementia patient because the earphone needs to be disposed within the earhole of the patient. Accordingly, the acoustic stimulation part 120 may be implemented as an osteophone and mounted around an ear, and may be implemented in a headphone form.

The device 100 for relieving dementia symptoms can minimize inconvenience attributable to wearing, and can also effectively relieve dementia through only the wearing of the device without the need for a separate behavior of a patient.

Figure 3:
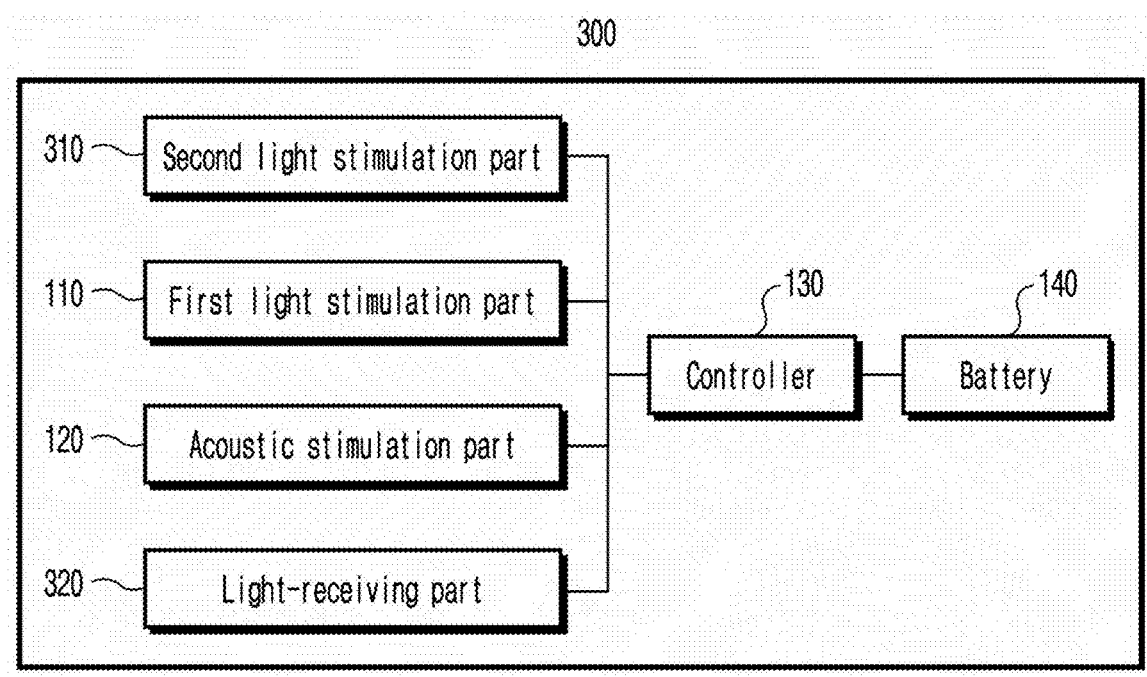
FIG. 3 is a diagram illustrating a construction of a device for relieving dementia symptoms according to a second embodiment of the present disclosure.

FIG. 3 is a diagram illustrating a construction of a device for relieving dementia symptoms according to a second embodiment of the present disclosure.

Referring to FIG. 3, a device 300 for relieving dementia symptoms according to the second embodiment of the present disclosure further includes a second light stimulation part 310 and a light-receiving part 320 in addition to the components of the device 100 for relieving dementia symptoms.

Like the first light stimulation part 110, the second light stimulation part 310 is attached to the middle of the forehead of a patient or a portion around the middle of the forehead, and radiates light to the optic nerve and frontal lobe of the patient. In order to accurately check the tissue activity of the patient, the second light stimulation part 310 is attached to the middle of the forehead of the patient, and radiates light to the body of the patient.

The second light stimulation part 310 radiates light having the near-infrared ray wavelength band. The light having the near-infrared ray wavelength band has properties in which the light is absorbed by hemoglobin. If much hemoglobin is included in the frontal lobe of a patient, the amount of light that is reflected by the frontal lobe is reduced because the amount of near-infrared light absorbed is increased. Hemoglobin is an oxygen carrier unless hemoglobin has special circumstances (e.g., carbon monoxide intoxication). In order to activate a specific tissue, hemoglobin must move to the specific tissue. Accordingly, the second light stimulation part 310 radiates light in order to measure the heart rate or oxygen saturation of a patient.

Like the first light stimulation part 110, the second light stimulation part 310 radiates near-infrared light having different wavelengths. The second light stimulation part 310 also includes two or more light sources. Any one of the two or more light sources radiates light having a wavelength band of about 730 nm, and another of the two or more light sources radiates light having a wavelength band of about 850 nm. The type of hemoglobin that moves to the frontal lobe of a patient includes oxy hemoglobin (Oxy Hb) for providing oxygen to the frontal lobe and deoxy hemoglobin (Deoxy Hb) that has already provided oxygen to the frontal lobe. At least two second light stimulation parts 310 radiate near-infrared light having different wavelengths so that the central processing unit 130 can derive concentrations of the oxy hemoglobin (Oxy Hb) and the deoxy hemoglobin (Deoxy Hb).

Furthermore, the second light stimulation part 310 radiates light having a frequency of 10 to 20 Hz. The first light stimulation part 110 radiates light having a preset frequency band (e.g., a gamma frequency band) for the purpose of a symptom relief object. In contrast, the second light stimulation part 310 radiates light, so that the light-receiving part 320 receives reflected light and the central processing unit 130 can analyze oxygen saturation. Accordingly, the second light stimulation part 310 needs to radiate light having a frequency, which can be smoothly received by the light-receiving part 320. Accordingly, the second light stimulation part 310 radiates light having a frequency of 10 to 20 Hz, not a gamma frequency band.

The plurality of light-receiving parts 320 is disposed to be spaced apart from the second light stimulation part 310 at a predetermined distance, and receives reflected light that is reflected by the artery within the skin or the frontal lobe of a patient.

The light-receiving part 320 may be disposed within a preset radius (e.g., several cm) from the second light stimulation part 310, and may be disposed in a plural number outside a preset radius. A distance between a light source and the light-receiving part 320 is proportion to a degree of light transmitted, which is radiated by the light source. If the light-receiving part 320 is disposed within the preset radius from the second light stimulation part 310, light that is reflected by the artery within the skin, not light that is incident up to the frontal lobe of a patient, is received by the light-receiving part 320. In contrast, if the light-receiving part 320 is disposed outside the preset radius from the second light stimulation part 310, light that is reflected after being incident up to the frontal lobe of the patient, may be received by the light-receiving part 320. Accordingly, the light-receiving part 320 may be disposed at a different location depending on a target whose oxygen saturation is to be measured.

The light-receiving part 320 receives reflected light by a preset number per time. The light-receiving part 320 receives reflected light that is reflected without being absorbed by hemoglobin, among pieces of near-infrared light radiated by the second light stimulation part 310. Each light-receiving part 320 transfers sensed information on the amount of reflected light to the central processing unit 130, so that the central processing unit 130 can derive a concentration (or oxygen saturation) of hemoglobin based on the amount of reflected light. In this case, each light-receiving part 320 may receive reflected light by a preset number per given time. For example, each light-receiving part 320 may receive reflected light 20 times per second.

Furthermore, the light-receiving parts 320 for receiving reflected light from the frontal lobe of a patient are disposed to face the left brain and right brain of the patient, respectively. Corresponding light-receiving parts 320 are not randomly disposed around the forehead (e.g., a location spaced apart from a light source at a given interval), but a given number of light-receiving parts are disposed to face the left brain and the remaining light-receiving parts are disposed to face the right brain. Corresponding light-receiving parts 320 may be disposed as described above, and may receive reflected light from both the left brain and the right brain. The central processing unit 130 can derive tissue activity, such as metabolic activity or oxygen saturation, based on data that is received by a corresponding light-receiving part 320, and can also check connectivity between the left brain and the right brain. Accordingly, higher accuracy for dementia diagnosis can be secured.

The central processing unit 130 controls operations of the first light stimulation part 110, the acoustic stimulation part 120, the second light stimulation part 310, and the light-receiving part 320. The central processing unit 130 of the device 300 controls the first light stimulation part 110 and the acoustic stimulation part 120 in the same manner as the central processing unit 130 of the device 100 for relieving dementia symptoms.

The central processing unit 130 controls an operation of the second light stimulation part 310. The central processing unit 130 controls the second light stimulation part 310 to radiate light having a frequency of 10 to 20 Hz. In controlling an operation of the second light stimulation part 310, the central processing unit 130 controls the second light stimulation part 310 to operate in an interval in which the first light stimulation part 110 does not operate so that the operation of the second light stimulation part 310 does not overlap an operation of the first light stimulation part 110. The second light stimulation part 310 may operate prior to an operation of the first light stimulation part 110 because the second light stimulation part 310 has an object of measuring oxygen saturation along with the light-receiving part 320.

The central processing unit 130 measures oxygen saturation of a patient based on the amount of reflected light that is received by the light-receiving part 320. The central processing unit 130 measures the heart rate or oxygen saturation of a patient from the artery within the skin of the patient, based on a value of the amount of reflected light that is received by the light-receiving part 320 disposed outside a preset radius from the second light stimulation part 310. The central processing unit 130 measures the patient's brain oxygen saturation based on a value of the amount of reflected light that is received by the light-receiving part 320 disposed outside the preset radius from the second light stimulation part 310.

Accordingly, the device 300 for relieving dementia symptoms can measure oxygen saturation in the patient's brain or artery, in addition to the relief of dementia symptoms.

FIG. 3 illustrates that the second light stimulation part 310 is further included, but the present disclosure is not limited thereto. The second light stimulation part 310 may be replaced as the frequency of a signal that is output by the light stimulation part 110 is changed under the control of the central processing unit 130.

Figure 4:
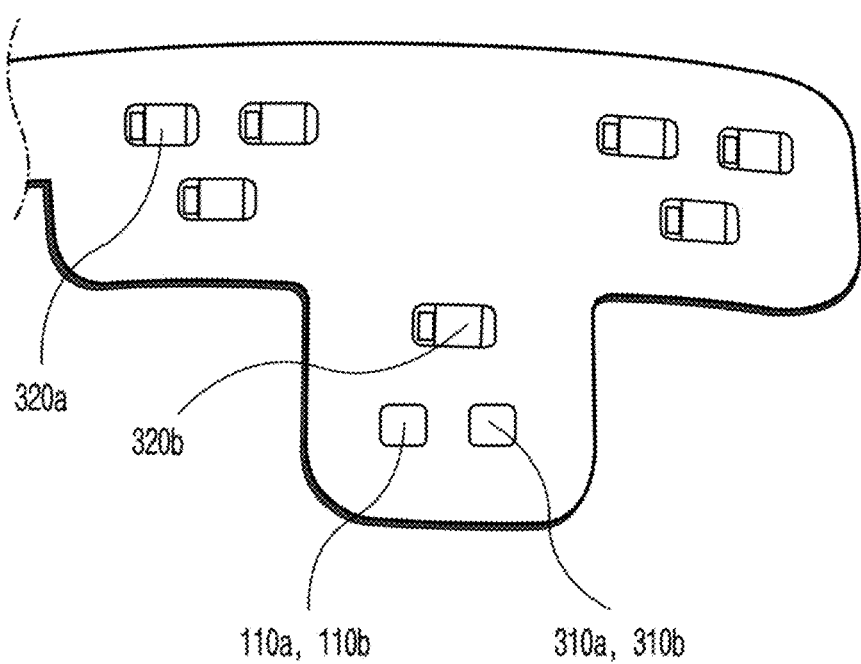
FIG. 4 is an exemplary diagram of a light stimulation part and a light-receiving part according to a second embodiment of the present disclosure.

FIG. 4 is an exemplary diagram of a light stimulation part and a light-receiving part according to a second embodiment of the present disclosure.

The device 300 for relieving dementia symptoms may be implemented in a form identical with a form of the device 100 for relieving dementia symptoms. In the device 100 for relieving dementia symptoms, only the light stimulation part 110 is disposed in the middle of the forehead of a patient or around the middle of the forehead. In contrast, in the device 300 for relieving dementia symptoms, the first and second light stimulation parts 110 and 310 and the light-receiving part 320 illustrated in FIG. 4 are disposed in the middle of the forehead of a patient or around the middle of the forehead.

The first light stimulation part 110 and the second light stimulation part 310 are disposed in the middle of the forehead of a patient or around the middle of the forehead. A light-receiving part 320*b* is disposed within a preset radius from the light stimulation parts 110 and 310. Only one light-receiving part 320*b* may be disposed as illustrated in FIG. 4, but two or more light-receiving parts 320*b* may be disposed.

Light-receiving parts 320*a* are disposed outside a preset radius from the light stimulation parts 110 and 310. As described above, the light-receiving parts 320*a* may be disposed in both a left brain portion and right brain portion of a patient, and may be disposed in a plural number. In particular, a total of six or more light-receiving parts 320*a* may be disposed so that the central processing unit 130 can measure oxygen saturation of the blood of the brain more accurately.

Furthermore, in FIG. 3, the light stimulation parts and the light-receiving parts have been disposed in a T-shaped form, but the present disclosure is not essentially limited thereto. The light stimulation parts and the light-receiving parts may be disposed in various forms other than a preset radius, such as that the light-receiving parts 320*a* are disposed in a fan-shaped form within the same radius on the basis of the light stimulation parts 110 and 310.

The above description is merely a description of the technical spirit of the present embodiment, and those skilled in the art may change and modify the present embodiment in various ways without departing from the essential characteristic of the present embodiment. Accordingly, the embodiments should not be construed as limiting the technical spirit of the present embodiment, but should be construed as describing the technical spirit of the present embodiment. The technical spirit of the present embodiment is not restricted by the embodiments. The range of protection of the present embodiment should be construed based on the following claims, and all of technical spirits within an equivalent range of the present embodiment should be construed as being included in the scope of rights of the present embodiment.

What is claimed is:

1. A device for relieving dementia symptoms, comprising:
   a first light stimulation part configured to be disposed at a location within a preset radius from an eyeball and frontal lobe of a patient and configured to radiate light having a preset wavelength band to an optic nerve and frontal lobe of the patient;
   an acoustic stimulation part configured to stimulate a brain of the patient by outputting a sonorant having a gamma frequency band;
   a second light stimulation part configured to be mounted within a location within the preset radius from the eyeball and frontal lobe of the patient and configured to radiate, light having the preset wavelength band, to the optic nerve and frontal lobe of the patient;
   a first light-receiving part disposed within a preset radius from the second light stimulation part and configured to receive light that is reflected by an artery within a skin of the patient after being radiated by the first and second light stimulation parts; and
   a plurality of second light-receiving parts disposed outside a preset radius from the second light stimulation part and configured to receive light that is reflected by the frontal lobe of the patient after being radiated by the first and second light stimulation parts,
   wherein a central processing unit is configured to control an operation of the first light stimulation part, the second light stimulation part, and the acoustic stimulation part,
   wherein some of the plurality of second light-receiving parts are disposed to be directed toward a left brain of the patient and remaining of the plurality of second light-receiving parts thereof are disposed to be directed toward a right brain of the patient so that the plurality of second light-receiving parts are able to receive all of a reflected light reflected by the left brain and the right brain, and
   the central processing unit synchronizes an optical signal that is output by the first and second light stimulation parts and an acoustic signal that is output by the acoustic stimulation part,
   wherein each of the first light stimulation part and the second light stimulation part includes a first light source configured to radiate a first light having a wavelength band of 730 nm, and
   a second light source configured to radiate a second light having a wavelength band of 850 nm, each of the first light stimulation part and the second light stimulation part outputs the first light and the second light alternately, a positive peak point of the sonorant has a phase between a phase synchronized with the first light output by the first light stimulation part and a phase synchronized with the second light output by the second light stimulation part, and a phase of the sonorant is adjusted based on an aspect of dementia symptoms of the patient.

2. The device of claim 1, wherein the preset wavelength band is a near-infrared ray wavelength band.

3. The device of claim 1, wherein the first or second light stimulation part radiates light having a preset frequency band.

4. The device of claim 3, wherein the central processing unit is configured to change a frequency band of the light radiated by the first or second light stimulation part into a second preset frequency band.

5. The device of claim 4, further comprising the first light-receiving part disposed within a preset radius from the first or second light stimulation part and configured to receive the radiated first and second light in the second preset frequency band from the first or second light stimulation part, that is reflected by the artery within the skin of the patient.

6. The device of claim 5, wherein the central processing unit measures a heart rate and oxygen saturation of the patient based on information received by the first light-receiving part.

7. The device of claim 4, wherein the central processing unit measures a patient's brain oxygen saturation based on information received by the another second light-receiving part.

8. The device of claim 1, wherein the first light stimulation part is configured to radiate light having the preset frequency band between 30 Hz and 50 Hz, and the second light stimulation part is configured to radiate the light having the frequency band between 10 Hz and 20 Hz.

* * * * *